United States Patent
Gengler et al.

(10) Patent No.: US 11,622,849 B2
(45) Date of Patent: Apr. 11, 2023

(54) LENSES WITH OPTICAL MARKINGS

(71) Applicant: AMO Groningen B.V., Groningen (NL)

(72) Inventors: Régis Y. N. R Gengler, Groningen (NL); Theophilus T. Bogaert, Groningen (NL); Tjeerd Zuidema, Groningen (NL); Hendrik H. Bekkering, Groningen (NL)

(73) Assignee: AMO Groningen B.V., Groningen (NL)

( * ) Notice: Subject to any disclaimer, the term of this patent is extended or adjusted under 35 U.S.C. 154(b) by 375 days.

(21) Appl. No.: 16/265,549

(22) Filed: Feb. 1, 2019

(65) Prior Publication Data

US 2019/0231517 A1 Aug. 1, 2019

Related U.S. Application Data

(60) Provisional application No. 62/703,844, filed on Jul. 26, 2018, provisional application No. 62/625,269, filed on Feb. 1, 2018.

(51) Int. Cl.
*A61F 2/16* (2006.01)
*G02C 7/04* (2006.01)
*G02C 7/02* (2006.01)

(52) U.S. Cl.
CPC ............ *A61F 2/16* (2013.01); *G02C 7/021* (2013.01); *G02C 7/04* (2013.01);
(Continued)

(58) Field of Classification Search
CPC ............ A61F 2/16; A61F 2002/1683; A61F 2250/0085; A61F 2250/0086;
(Continued)

(56) References Cited

U.S. PATENT DOCUMENTS 4,039,827 A * 8/1977 Zdrok .................... G02C 7/021
 250/271
4,194,814 A 3/1980 Fischer et al.
(Continued)

FOREIGN PATENT DOCUMENTS

DE 102009056810 A1 6/2011
DE 102010052665 A1 5/2012
(Continued)

OTHER PUBLICATIONS

Malinauskas M., et al., "Fine Structuring of Integrated Micro-Optical Components Using Lasers," Article in SPIENewsroom, Jul. 2011, 23 Reads, DOI: 10.1117/2.1201107.003708.
(Continued)

*Primary Examiner* — Jerrah Edwards
*Assistant Examiner* — Aren Patel
(74) *Attorney, Agent, or Firm* — Johnson & Johnson Surgical Vision, Inc.

(57) ABSTRACT

A lens including a posterior surface, an anterior surface, and at least one identification marking on the lens. The at least one identification marking exhibits a first degree of visibility in an ambient lighting condition and a second degree of visibility greater than the first degree of visibility in a lighting condition different than the ambient lighting condition.

28 Claims, 8 Drawing Sheets

(52) U.S. Cl.
CPC ............... *A61F 2002/1683* (2013.01); *A61F 2250/0085* (2013.01); *A61F 2250/0086* (2013.01); *A61F 2250/0089* (2013.01); *A61F 2250/0097* (2013.01)

(58) Field of Classification Search
CPC ..... A61F 2250/0089; A61F 2250/0097; G02C 7/04; G02C 7/021
See application file for complete search history.

(56) References Cited

U.S. PATENT DOCUMENTS

| | | | |
|---|---|---|---|
| 4,219,721 A | 8/1980 | Bernfeld et al. | |
| 5,467,149 A | 11/1995 | Morrison et al. | |
| 5,538,674 A | 7/1996 | Nisper et al. | |
| 5,936,704 A | 8/1999 | Gabrielian et al. | |
| 6,042,230 A | 3/2000 | Neadle et al. | |
| 6,203,156 B1 | 3/2001 | Wu et al. | |
| 6,857,744 B2 | 2/2005 | Nakada et al. | |
| 7,708,401 B2 | 5/2010 | Sabeta | |
| 8,115,792 B2 | 2/2012 | Petsch et al. | |
| 8,313,793 B2 | 11/2012 | Nizienko | |
| 9,144,491 B2 | 9/2015 | Knox et al. | |
| 9,158,133 B1* | 10/2015 | Pletcher | G06K 7/10158 |
| 9,274,350 B2 | 3/2016 | Ochrombel et al. | |
| 9,277,988 B1* | 3/2016 | Chu | A61F 2/1613 |
| 9,566,749 B2 | 2/2017 | Van Dijk | |
| 2004/0240006 A1 | 12/2004 | Staub et al. | |
| 2006/0235428 A1* | 10/2006 | Silvestrini | A61F 2/15 606/107 |
| 2007/0052876 A1* | 3/2007 | Kaufman | G02B 3/14 349/13 |
| 2009/0006017 A1 | 1/2009 | Young et al. | |
| 2009/0204207 A1* | 8/2009 | Blum | A61F 2/1613 623/4.1 |
| 2009/0302122 A1* | 12/2009 | Begon | G03H 1/02 235/494 |
| 2011/0089585 A1 | 4/2011 | Biel et al. | |
| 2011/0118836 A1* | 5/2011 | Jain | A61F 2/16 623/6.27 |
| 2014/0199521 A1 | 7/2014 | Carpenter | |
| 2015/0347887 A1* | 12/2015 | Vosoogh-Grayli | G06K 7/10821 235/454 |
| 2016/0070999 A1* | 3/2016 | Pranov | B29C 33/428 235/462.11 |
| 2016/0143728 A1* | 5/2016 | De Smet | G02C 7/04 623/6.22 |
| 2016/0207249 A1 | 7/2016 | Maurice et al. | |

FOREIGN PATENT DOCUMENTS

| | | |
|---|---|---|
| EP | 0291459 A2 | 11/1988 |
| EP | 1158339 A1 | 11/2001 |
| EP | 0865616 B1 | 3/2002 |
| EP | 1887414 A1 | 2/2008 |
| EP | 3139201 A1 | 3/2017 |
| EP | 3255416 A1 | 12/2017 |
| WO | 9810324 A1 | 3/1998 |

OTHER PUBLICATIONS

International Search Report and Written Opinion for Application No. PCT/IB2019/050821, dated May 3, 2019, 17 pages.

* cited by examiner

LENSES WITH OPTICAL MARKINGS

CROSS-REFERENCE TO RELATED APPLICATIONS

This application claims the benefit under 35 U.S.C. § 119(e) of U.S. Provisional Patent Application Nos. 62/625,269, filed Feb. 1, 2018 and 62/703,844, filed Jul. 26, 2018, both of which are incorporated herein by reference in their entirety.

FIELD

The present disclosure relates generally to lens markings.

BACKGROUND

There are a variety of different types of ophthalmic lenses (e.g., monofocal intraocular lenses (IOL), multifocal IOLs, accommodating IOLs, and toric IOLs) and each type of ophthalmic lens may have a variety of different optical properties (e.g., power (diopters), zonal information, axis of the flat meridian). Because the ophthalmic lens type and the optical properties of the ophthalmic lens are not readily apparent by visual inspection of the lens, unique identifiers are commonly utilized to indicate the various properties of the ophthalmic lens. Many conventional ophthalmic lenses, however, do not include unique identifiers provided directly on the lenses themselves. Instead, the unique identifiers are typically provided on a container storing the lens. Once the lens becomes separated from the container that holds the lens, it may be difficult or impossible to determine the optical properties, the manufacturing process (e.g., process identifiers and serial number), and/or other characteristics of the lens. Accordingly, when two or more conventional lenses are removed from their containers, these lenses are susceptible to being inadvertently switched.

Additionally, because conventional ophthalmic lenses are not directly marked with a unique identifier, certain manufacturing processes, such as a batch process in which the lenses are not confined or fixed in place (e.g., a tumble polish process), are unsuitable for producing different lens types or lenses having different optical properties in the same batch because the unique properties or characteristics of the lenses cannot be tracked.

Some conventional ophthalmic lenses may include a marking for identifying various properties of the ophthalmic lens. However, many conventional markings on ophthalmic lenses negatively affect the optical properties of the lens. Additionally, conventional markings on ophthalmic lenses formed by laser engraving are typically limited to simple structures such as holes (e.g., pits) depleted from the anterior or posterior surface of the lens or simple structures formed in a bulk portion of the lens between the anterior or posterior surfaces (e.g., bubbles) to induce a refractive index change in the lens at the marking.

SUMMARY

The present disclosure is directed to various embodiments of lens. In one embodiment, the lens includes a posterior surface, an anterior surface, and at least one identification marking on or inside the lens. The at least one identification marking exhibits a first degree of visibility in an ambient lighting condition and a second degree of visibility greater than the first degree of visibility in a lighting condition different than the ambient lighting condition. The first degree of visibility may be substantially no visibility.

The at least one identification marking may include a micro-structure engraving or a nano-structure engraving.

The lighting condition may include incident light having a wavelength, and the at least one identification marking may include a phase plate defined in or on at least one of the posterior surface, the anterior surface, a perimeter of the lens, or a bulk portion of the lens between the anterior and posterior surfaces. The phase plate may have a depth substantially equal to the wavelength of the incident light or less than the wavelength of the incident light. The phase plate may be configured to phase shift the incident light, and the phase shift may be detectable by an interferometer.

The at least one identification marking may include a flat surface and a tapered indent, and the lighting condition may include polarized light angled at Brewster's angle with respect to the flat surface. The tapered indent may include a step and a slanted surface. The slanted surface of the tapered indent may be configured to reflect the polarized light, and the flat surface may be configured not to reflect the polarized light.

The at least one identification marking may include a retro-reflector, a pyramidal reflector, and/or a diffraction grating.

In one embodiment, the lens includes a posterior surface, an anterior surface, and at least one identification marking on the lens. The at least one identification marking may include a pattern of features having at least one periodicity resolvable in Fourier space. The pattern may be an array.

The at least one periodicity may include a series of different periodicities.

Each feature of the pattern of features may be a micro-structure engraving or a nano-structure engraving.

Each feature of the pattern of features may be a line or a dot.

In one embodiment, the lens includes a posterior surface, an anterior surface, a matrix including a series of cells configured to encode identification information of the lens, and at least one identification marking in at least one cell of the series of cells. The at least one identification marking includes a micro-structure engraving or nano-structure engraving.

The at least one identification marking may include a phase plate, a flat surface and a tapered indent, a retro-reflector, a pyramidal reflector, a diffraction grating, and/or a pattern of features having at least one periodicity resolvable in Fourier space. The at least one identification marking may be provided on an anterior surface of the lens, a posterior surface of the lens, a perimeter of the lens, or in a bulk portion (e.g., an interior) of the lens between the anterior and posterior surfaces.

Each cell of the series of cells in the matrix may represent a binary digit of the encoded identification information. In one embodiment, each cell without an identification marking represents a value of 0, and each cell including at least one identification marking represents a value of 1. In another embodiment, each cell without an identification marking represents a value of 1, and each cell including at least one identification marking represents a value of 0.

At least one cell of the series of cells that includes the at least one identification marking may represent a non-binary value of the encoded identification information. The non-binary value may be in a range from 0 to 1, a range from 0 to $2\pi$ radians, a range from 0 to 100, or a range from 1 to 256.

At least one cell of the series of cells may include a super-structure. The super-structure includes a series of sub-cells.

The lens may include a first type of identification marking in one cell of the series of cells and a second type of identification marking different than the first type of identification marking in another cell of the plurality of cells.

The identification marking may include human readable text or machine readable text.

The lens may include a series of identification markings. A first identification marking of the series of identification markings may be at least partially aligned with a second identification marking of the series of identification markings along an axis parallel to an optical axis of the lens, and the first identification marking and the second identification markings may be at different positions along the axis.

This summary is provided to introduce a selection of features and concepts of embodiments of the present disclosure that are further described below in the detailed description. This summary is not intended to identify key or essential features of the claimed subject matter, nor is it intended to be used in limiting the scope of the claimed subject matter. One or more of the described features may be combined with one or more other described features to provide a workable device.

BRIEF DESCRIPTION OF THE DRAWINGS

These and other features and advantages of embodiments of the present disclosure will become more apparent by reference to the following detailed description when considered in conjunction with the following drawings. In the drawings, like reference numerals are used throughout the figures to reference like features and components. The figures are not necessarily drawn to scale.

DETAILED DESCRIPTION

The present disclosure is directed to various embodiments of a lens including at least one marking for identifying one or more characteristics of the lens (e.g., optical properties of the lens, such as intraocular lens (IOL) type, power range, spherical equivalent (SE), cylinder power (Cyl), axis, spherical aberration (SA), and/or zonal information), a manufacturing process of the lens, and/or customer information (e.g., identification of the surgeon, the clinic, the patient, and/or a shipping address). The at least one marking of the lens may be utilized to facilitate placement of the lens on or in the eye of a patient. For instance, the at least one marking on the lens may be utilized by a surgeon to facilitate the alignment of toric IOLs in a patient or may be utilized by a surgeon to localize haptics of the lens in the eye of a patient. In one or more embodiments, the one or more markings may be provided on a contact lens to indicate to a user the proper orientation of the contact lens (e.g., the front and back surfaces of the contact lens). The one or more markings on the lens may be a computer-readable marking and/or a human readable marking. The markings according to various embodiments of the present disclosure are micro- or nano-structure etchings or engravings. The micro- or nano-structure etchings of the present disclosure may be formed on a posterior surface of the lens, an anterior surface of the lens, an interior portion of the lens between the anterior and posterior surfaces (e.g., a bulk portion of the lens), an outer periphery (e.g., a perimeter or edge) of the lens, and/or on a haptic of the lens. The markings according to one or more embodiments of the present disclosure are configured to be visible and readable under predefined conditions (e.g., refractive indices) and/or predefined light settings (e.g., a predefined angle of incidence, polarization, and/or wavelength of the light incident on the marking) and to have a reduced visibility (e.g., invisible or substantially invisible) under standard (e.g., ambient) lighting conditions. In one or more embodiments, the markings according to one or more embodiments of the present disclosure may be visible and readable after implantation in the eye of a patient.

With reference now to FIGS. 1A-1F, a lens 100 according to various embodiments of the present disclosure includes an optic 101 and a pair of haptics 102, 103 extending outward from the optic 101 to localize the optic 101 in the capsular bag of a patient's eye. In one or more embodiments, the haptics 102, 103 may have any other suitable configuration. In one or more embodiments, the lens 100 may be any suitable type or kind of ophthalmic lens, such as a pseudophakic IOL, a phakic IOL (PIOL), an aphakic IOL, or a toric IOL. In one or more embodiments, the lens 100 may be an accommodating IOL configured to change the focus of the optic due to contraction and relaxation of the ciliary muscles in the patient's eye acting on the haptics 102, 103 (e.g., vaulting of the anterior surface and/or the posterior surface of the optic 101 in response to contraction of the patient's ciliary muscles).

Figure 1A:
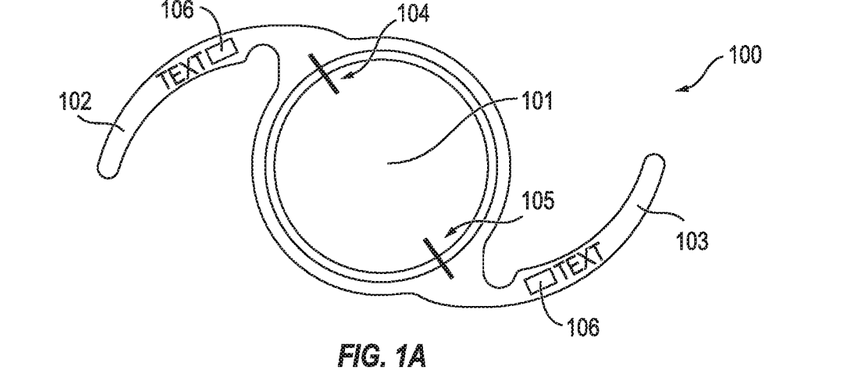
FIGS. 1A-1F are front views of a lens including at least one marking according to various embodiments of the present disclosure.
Figure 1B:
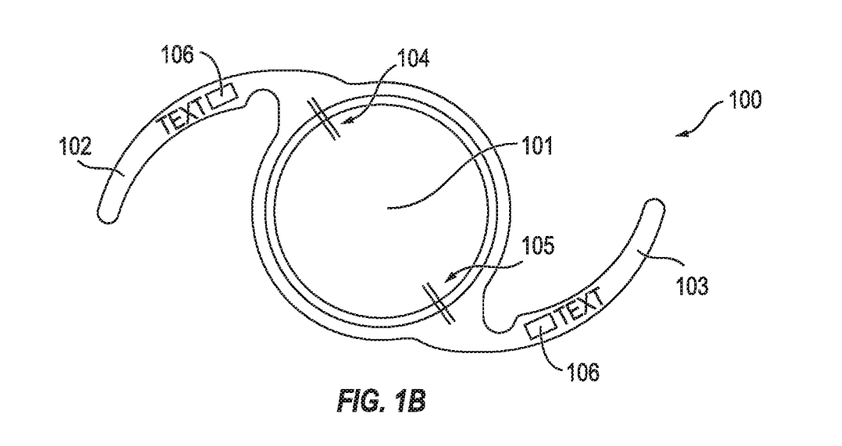
Figure 1C:
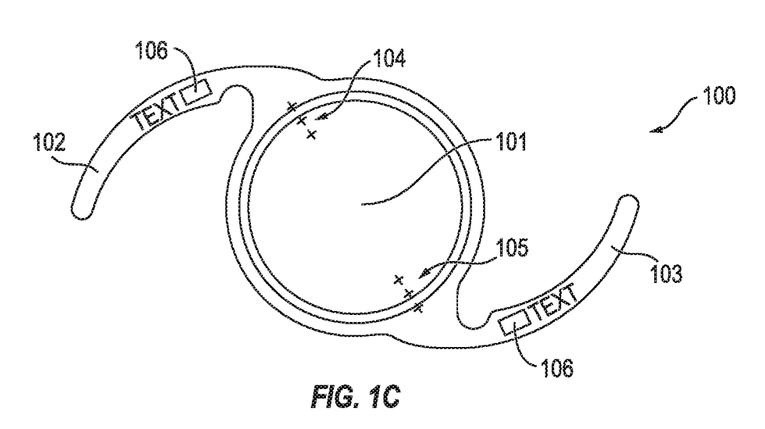
Figure 1D:
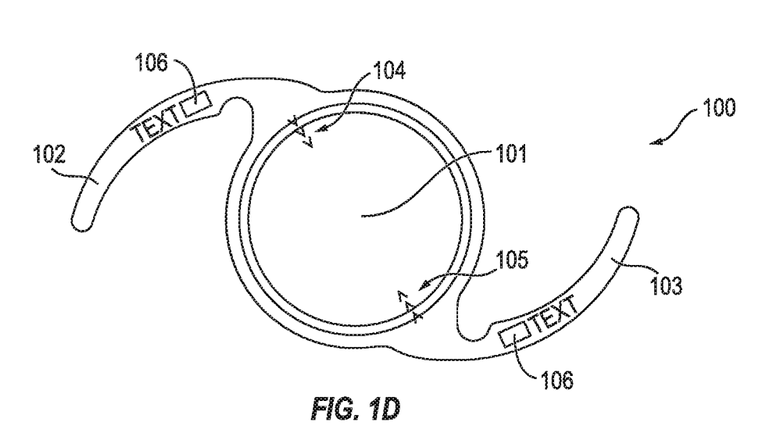

In one or more embodiments in which the lens 100 is a toric IOL, the toric IOL may include an opposing pair or set of markings 104, 105 configured to enable a surgeon to align the toric IOL with the patient's pre-existing corneal astigmatism axis (e.g., enable alignment of the toric IOL inside the eye of a patient on a meridian that corrects the pre-existing astigmatism). In the illustrated embodiments, the markings 104, 105 configured to enable alignment of the toric IOL may include a pair of opposing radial line segments (FIG. 1A), a pair of opposing parallel line segments (FIG. 1B), at least one pair of opposing plus symbols (FIG. 1C), or at least one pair of opposing arrow symbols oriented radially inward toward the optical axis of the optic (FIG. 1D). Together, the opposing pair of markings 104, 105 define an axis of the toric IOL (e.g., an axis defining a flat meridian of the toric IOW that is configured to be aligned with the patient's pre-existing astigmatism axis during implantation of the toric IOL. In one or more embodiments, the markings 104, 105 configured to enable alignment of the toric IOL may have any other suitable shape or combination of shapes. In one or more embodiments, the markings 104, 105 may include one or more characters (e.g., human readable text), In one or more embodiments, the markings 104, 105 may contain additional Information (e.g., identification codes identifying the optical characteristics of the lens 100, a manufacturing process of the lens 100, and/or customer information). For Instance, in one or more embodiments in which the markings 104, 105 contain additional information, the additional information may be encoded in the markings 104, 105 themselves (e.g., the markings 104, 105 may be a matrix of dots encoding the additional information) or the additional information may be provided between the markings 104, 105 (e.g., the additional information may be provided between the parallel lines segments of the markings 104, 105 shown in FIG. 1B). In one or more embodiments in which the lens 100 is not a toric IOL (e.g., a spherical IOL), the lens 100 may be provided without the markings 104, 105.

Additionally, in the illustrated embodiments, the lens 100 also includes at least one identification marking 106 for identifying one or more characteristics of the lens 100 (e.g., a serial number and/or optical properties, such as intraocular lens (IOL) type, power range, spherical equivalent (SE), cylinder power (Cyl), axis, spherical aberration (SA), and/or zonal information), a manufacturing process of the lens, and/or customer information (e.g., identification of the surgeon, the clinic, the patient, and/or a shipping address). In the illustrated embodiment, the one or more markings 106 for identifying one or more characteristics of the lens 100 are provided on the haptics 102, 103 (e.g., one identification marking on each of the two haptics 102, 103). In one or more embodiments, the one or more identification markings 106 may be provided in any other suitable location on the lens 100, such as at a peripheral portion of the optic 101. Additionally, in one or more embodiments, the one or more identification markings 106 may be provided on an anterior surface of the optic 101, on a posterior surface of the optic 101, on an outer periphery (e.g., a perimeter or edge) of the optic 101, or in a bulk portion of the lens between the anterior and posterior surfaces. In one or more embodiments, the identification markings 106 may be provided on two symmetric locations on the lens 100 (e.g., symmetric locations on the haptics 102, 103 or opposing locations on the periphery of the optic 101). Providing the markings 106 on two symmetric locations on the lens 100 is configured to reduce processing times (e.g., by enabling reading, such as scanning, of either one of markings 106) and also provide redundancy. Although in one or more embodiments the one or more identification markings 106 may have a rectangular outline, in one or more embodiments the identification markings 106 may have a non-rectangular outline. For instance, in one or more embodiments, one or more of the identification markings 106 may be curved (e.g., in one or more embodiments in which the identification markings 106 are provided on the haptics 102, 103, the one or more of the identification markings 106 may have a curvature matching or substantially matching a curvature of the haptics 102, 103). Suitable configurations for the one or more identification markings 106 are described below with reference to the embodiments depicted in FIGS. 2-8B.

Figure 1E:
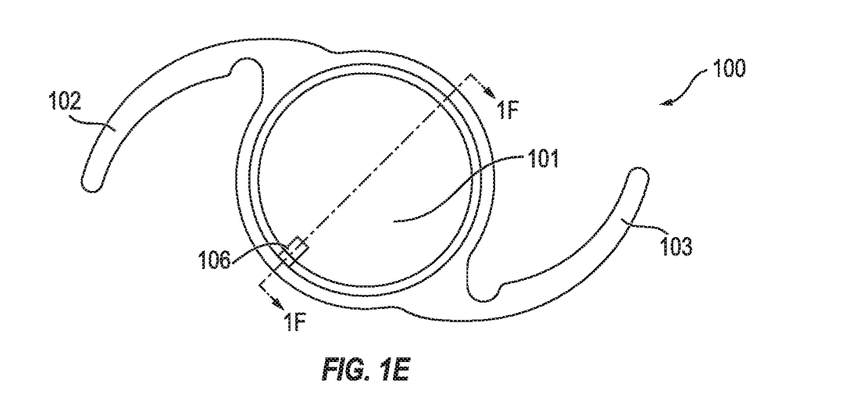
Figure 1F:
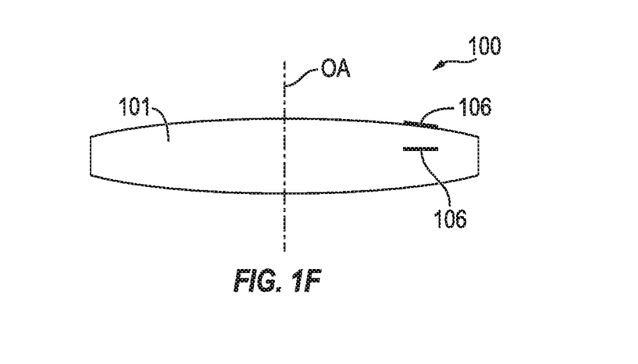

FIGS. 1E-1F depict an embodiment of the lens 100 including two or more identification markings 106 at least partially overlapping each other when viewed in a direction parallel to the optical axis OA of the lens 100. For instance, in one or more embodiments, the lens 100 may include two or more identification markings 106 that are aligned or at least partially aligned along an axis parallel to the optical axis OA of the lens 100 but are located at different positions (e.g., depths) along the axis parallel to the optical axis OA of the lens 100. The focus capability of a microscope or other suitable instrument may be utilized to independently read the at least partially overlapping identification markings 106 (e.g., the focal length of the microscope or other instrument may be adjusted to differentiate the Identification markings 106 and read a desired one of the markings 106). In one or more embodiments, the lens 100 may include two or more identification markings 106 within the bulk portion of the optic 101 or within the bulk portion of one or more of the haptics 102, 103 that at least partially overlap each other when viewed in a direction parallel to the optical axis OA of the lens 100 (e.g., the lens 100 may include one identification marking 106 in the bulk portion of the optic 101 proximate to the anterior surface of the optic 101 and one identification marking 106 in the bulk portion of the optic 101 proximate to the posterior surface of the optic 101 that is aligned or at least partially aligned along an axis parallel to the optical axis OA with the identification marking 106 proximate to the anterior surface of the lens 100). In one or more embodiments, the lens 100 may include at least a first Identification marking 106 on the anterior surface or the posterior surface of the optic 100, and a second identification marking 106 in the bulk portion of the optic 100 that is aligned or at least partially aligned with the Identification marking 106 on the anterior or posterior surface. In one or more embodiments, the lens 100 may include a first identification marking 106 on the anterior surface of the optic 101 and a second identification marking 106 on the posterior surface of the lens 100 that is aligned or substantially with the first identification marking 106 on the anterior surface of the optic 101.

In one or more embodiments, the haptics 102, 103 may include one or more markings for increasing visibility of the haptics 102, 103 during implantation. Increasing the visibility of the haptics 102, 103 may assist or aid a surgeon in properly localizing the lens 100 in the capsular bag of the patient's eye during implantation. In one or more embodiments, the one or more markings for increasing the visibility of the haptics 102, 103 may also encode information about one or more characteristics of the lens 100. In one or more embodiments, the one or more markings for increasing the visibility of the haptics 102, 103 may be separate from the one or more identification markings encoding information about one or more characteristics of the lens 100.

In one or more embodiments, the identification markings 106 may include text (e.g., human readable text and/or computer readable text). In one or more embodiments in which the identification markings 106 include human readable text and/or machine readable text, the identification markings 106 may be provided on the haptics 102, 103 and/or on any other suitable portion of the lens 100, such as a peripheral portion of the lens 100.

Figure 2:
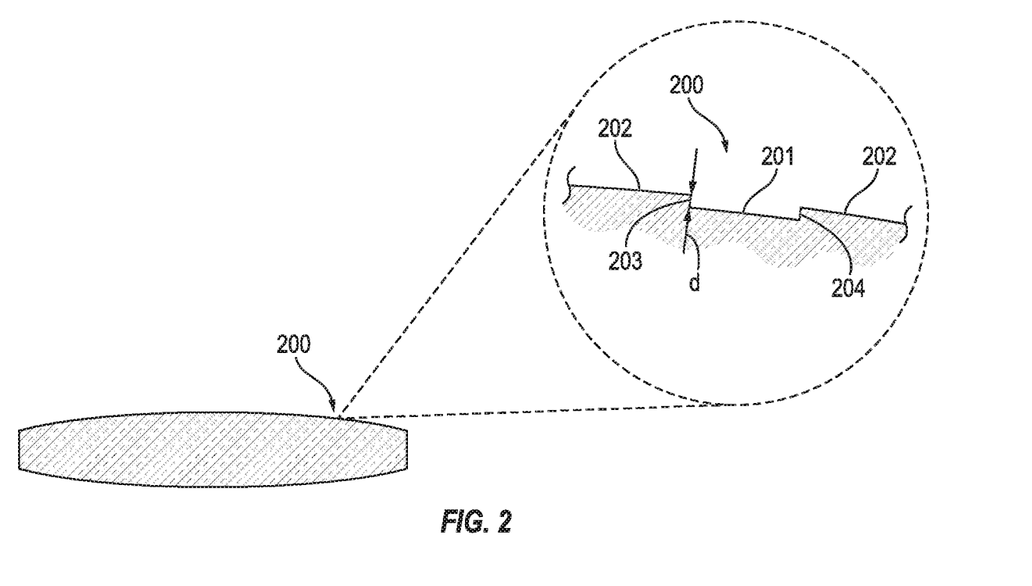
FIG. 2 is a cross-sectional view of a lens including a phase plate marking according to one embodiment of the present disclosure.

With reference now to FIG. 2, an identification marking 200 according to one embodiment of the present disclosure is an engraved micro- or nano-structure having a surface 201 recessed from a surface 202 (e.g., an anterior surface, a posterior surface, or a peripheral surface) of the lens and a pair of steps 203, 204 connecting or transitioning opposite ends of the recessed surface 201 to the surface of the lens 202. In one or more embodiments, the steps 203, 204 may have a step height equal or substantially equal to a predetermined wavelength of incident light that may be utilized to read or reveal the identification marking 200 (e.g., the recessed surface 201 may be recessed from the surface 202 of the lens by a depth d equal or substantially equal to the predetermined wavelength of incident light that may be utilized to read or reveal the identification marking 200). In one or more embodiments, the depth d of the recessed surface 201 may be less than the predetermined wavelength of the incident light (e.g., the recessed surface 201 may have a subwavelength depth that is a fraction of the predetermined wavelength of the incident light). In one or more embodiments, the depth d of the recessed surface 201 may be any fractional multiple of the predetermined wavelength of the incident light. Additionally, in one or more embodiments, the recessed surface 201 may be a gradient surface such that the depth d varies along the length of the recessed surface 201. In one or more embodiments, the at least one identification marking 200 may be formed in an anterior surface and/or a posterior surface of the lens and the depth d of the recessed surface 201 is measured from the anterior or posterior surface on which the identification marking 200 is located. In one or more embodiments, the at least one identification marking 200 may be formed in an interior (e.g., bulk portion) of the lens between the anterior and posterior surfaces. In one or more embodiments, the at least one identification marking 200 may be formed in outer periphery (e.g., a perimeter or edge) of the lens.

The identification marking 200 is configured to function as a phase plate. For instance, when incident light having the predetermined wavelength is incident on the identification marking 200, the recessed surface 201, which has a depth d less than or equal or substantially equal to the predetermined wavelength of the incident light, is configured to induce a phase shift in the incident light due to the greater distance that the incident light must travel to reach the recessed surface 201 compared to the surrounding surface 202 of the lens. The identification marking 200 is configured to induce a phase shift in both a transmission and a reflection of the incident light. The naked human eye is not sensitive to phase shifts of a light wave front (e.g., the naked human eye cannot discern or perceive phase shifts in a light wave front) and therefore the embodiment of the identification marking 200 illustrated in FIG. 2 is invisible to the naked human eye. The identification marking 200 on the lens may be revealed by directing light having the predetermined wavelength on the lens and utilizing an interferometer (e.g., an interferometric optical device) to observe the phase difference induced in the incident light by the recessed surface 201 of the identification marking 200. The phase shift in radians ($\Delta\varphi$) that the identification marking 200 is configured to induce in the incident light is defined by $\Delta\varphi = 2\pi d/\lambda$, where d is the depth of the recessed surface 201 and $\lambda$ is the wavelength of the incident light. Accordingly, the identification marking 200 is configured to induce a phase shift in the incident light between 0 and $2\pi$ radians depending on the depth d of the recessed surface 201 of the identification marking 200 relative to the wavelength of the incident light. In one or more embodiments, the identification marking 200 may represent a value in any other range of values (e.g., the identification marking 200 may represent any value in a color scale from 0 to 256 or the identification marking may represent any value in a scale from 0 to 100). This embodiment of the marking is referred to herein as the "phase plate marking."

Figure 3:
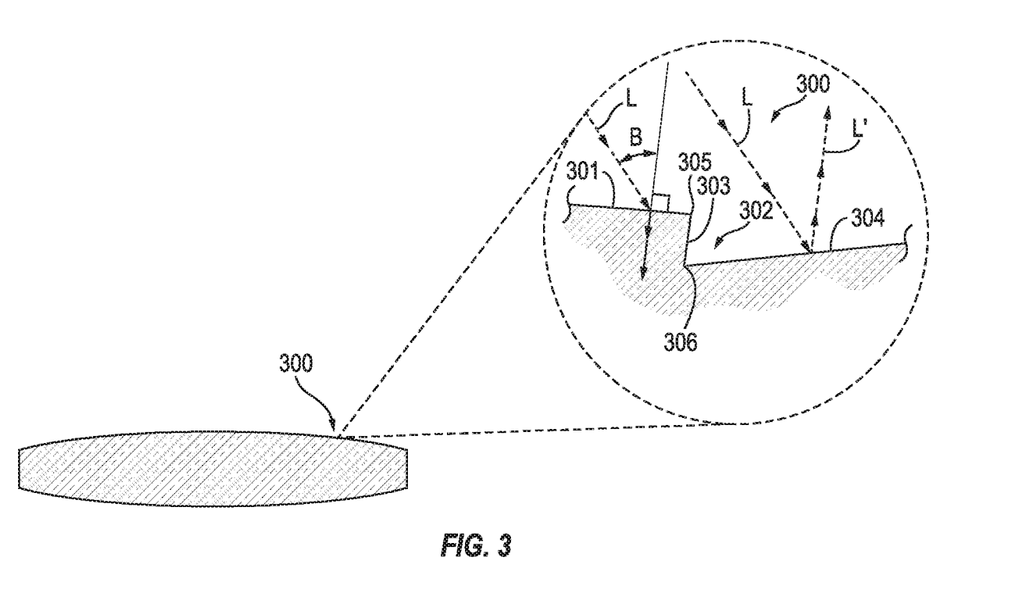
FIG. 3 is a cross-sectional view of a lens including a Brewster angle marking according to one embodiment of the present disclosure.

With reference now to FIG. 3, an identification marking 300 according to one embodiment of the present disclosure includes an engraved micro- or nano-structure including a flat or substantially flat surface 301 and a tapered indent 302. In one or more embodiments, the flat surface 301 may be perpendicular or substantially perpendicular to the optical axis of the lens. In the illustrated embodiment, the tapered indent 302 is defined by a step 303 and a slanted or sloped surface 304. An outer end 305 of the step 303 meets the flat surface 301 and the step 303 extends inward from the flat surface 301 along the optical axis of the lens. The sloped surface 304 extends outward from an inner end 306 of the step. In one or more embodiments, the at least one identification marking 300 may be formed in an anterior surface and/or a posterior surface of the lens. In one or more embodiments, the at least one identification marking 300 may be formed in an interior (e.g., bulk portion) of the lens between the anterior and posterior surfaces. In one or more embodiments, the at least one identification marking 300 may be formed in outer periphery (e.g., a perimeter or edge) of the lens.

The identification marking 300 on the lens may be revealed by directing incident light L at the identification marking 300 oriented at Brewster's angle $\beta$ relative to an axis perpendicular to the flat surface 301 of the identification marking 300. Brewster's angle $\beta$ is defined as the angle of incidence at which light having a particular polarization (e.g., perfectly p-polarized light) is perfectly or completely transmitted through the lens with no reflection. Accordingly, when the light L (e.g., perfectly p-polarized light) oriented at Brewster's angle $\beta$ is incident on the identification marking 300, the flat segment 301 will not reflect any light (e.g., the light L will be perfectly or substantially perfectly transmitted through the flat segment 301), but the sloped surface 304 of the tapered indent 302 will reflect light L'. In this manner, a user may differentiate between marked and unmarked areas of the lens (e.g., a user may distinguish between the flat surface 301 of the lens and the sloped surface 304 of the tapered indent 302). This embodiment of the identification marking is referred to herein as the "Brewster angle marking."

Figure 4:
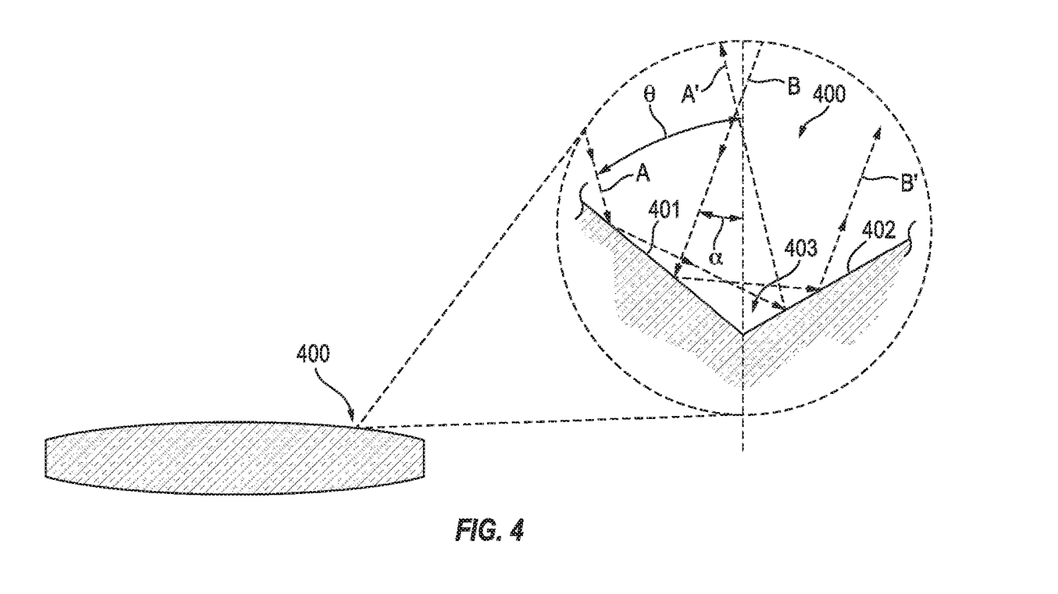
FIG. 4 is a cross-sectional view of a lens including a retro-reflector marking according to one embodiment of the present disclosure.

With reference now to FIG. 4, an identification marking 400 according to one embodiment of the present disclosure includes an engraved micro- or nano-structure including at least one pair of angled reflective surfaces or segments 401, 402 defining at least one wedge-shaped retro-reflector 403. In one or more embodiments, the at least one retro-reflector 403 may be formed in an anterior surface of the lens, a posterior surface of the lens, an outer periphery (e.g., a perimeter or edge) of the lens, and/or a bulk portion of the lens between anterior and posterior surfaces. The identification marking 400 is configured to reflect light incident on the retro-reflector 403 along a vector that is parallel but opposite in direction (e.g., having an opposite sense) to the angle of incidence of the incident light. In the illustrated embodiment, the identification marking 400 is configured to reflect light back toward its source when the angle of incidence of the incident light is greater than zero with respect to a line of symmetry of the retro-reflector. For instance, as illustrated in FIG. 4, when a light ray A is incident on the retro-reflector 403 at an angle of incidence $\theta$ with respect to the line of symmetry of the retro-reflector 403, the retro-reflector 403 reflects a light ray A' at the same angle of incidence $\theta$ as the light ray A but in a direction opposite to the light ray A. Similarly, when a light ray B is incident on the retro-reflector 403 at an angle of incidence $\alpha$ with respect to the line of symmetry of the retro-reflector 403, the retro-reflector 403 reflects a light ray B' at the same angle of incidence α as the light ray B but in a direction opposite to the light ray B. The presence of the identification marking 400 on the lens may be revealed or determined by directing incident light toward the retro-reflector 403 at a non-zero angle of incidence with respect to the line of symmetry, and detecting (e.g., viewing or measuring) light reflected from the retro-reflector 403 back toward the source of the incident light. This embodiment of the identification marking is referred to herein as the "retro-reflector marking."

Figure 5:
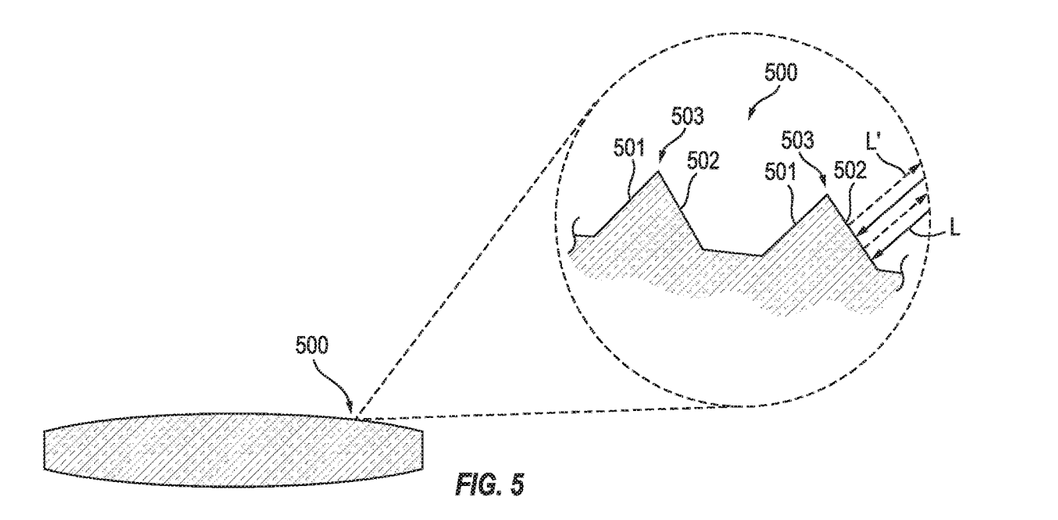
FIG. 5 is a cross-sectional view of a lens including a pyramidal reflector marking according to one embodiment of the present disclosure.

With reference now to FIG. 5, an identification marking 500 according to one embodiment of the present disclosure includes an engraved micro- or nano-structure including at least a pair of angled reflective segments or surfaces 501, 502 defining at least one pyramidal reflector 503. In one or more embodiments, the at least one pyramidal reflector 503 may be formed in or on an anterior surface, a posterior surface, an outer periphery (e.g., a perimeter or edge), or an interior (e.g., bulk portion) of the lens between the anterior and posterior surfaces. In one or more embodiments, the pair of angled reflective segments 501, 502 of the one or more pyramidal reflectors 503 project beyond or from a surface (e.g., the anterior surface, the posterior surface, or the perimeter) of the lens. In one or more embodiments, the pair of angled reflective segments 501, 502 of the one or more pyramidal reflectors 503 may be recessed relative to a surface (e.g., the anterior surface, the posterior surface, or the perimeter) of the lens. The identification marking 500 is configured to reflect light L incident on the pyramidal reflector 503 at an angle of incidence perpendicular or substantially perpendicular to one of the reflective surfaces 501, 502 of the pyramidal reflector 503 back toward the source of the incident light L. The presence of the at least one identification marking 500 on the lens may be revealed or determined by directing incident light L toward the pyramidal reflector 503 at an angle of incidence that is perpendicular or substantially perpendicular to one of the reflective surfaces 501, 502 of the pyramidal reflector 503, and detecting (e.g., viewing or measuring) light L' reflected from the pyramidal reflector 503 back toward the source of the incident light L. This embodiment of the identification marking is referred to herein as the "pyramidal reflector marking."

Figure 6:
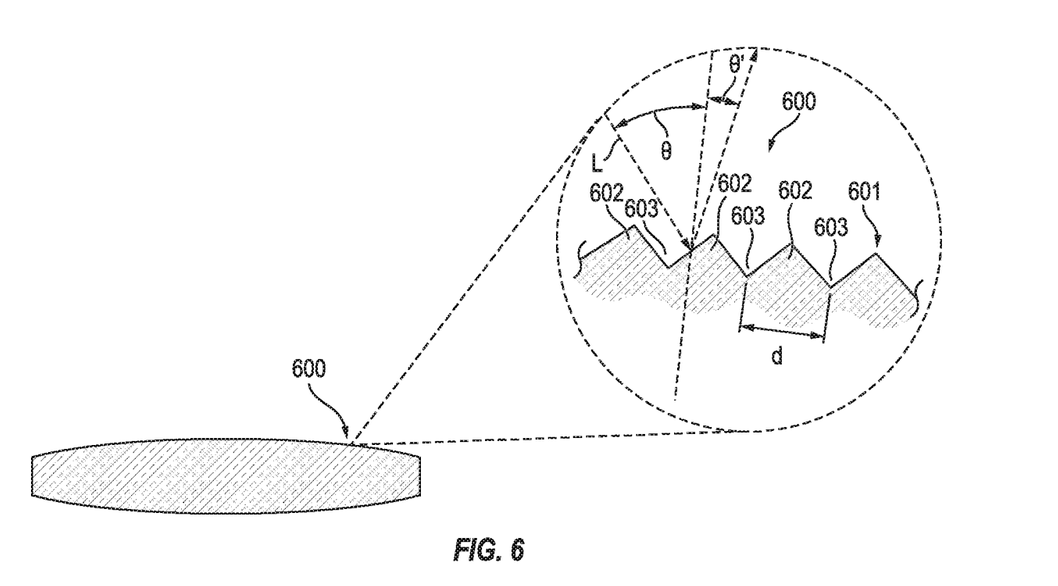
FIG. 6 is a cross-sectional view of a lens including a grating marking according to one embodiment of the present disclosure.

With reference now to FIG. 6, an identification marking 600 according to one embodiment of the present disclosure includes a grating structure 601 including a series of gratings 602 having a constant or substantially constant periodicity d (e.g., spacing). The gratings 602 define a series of grooves 603. In one or more embodiments, the periodicity d of the grating structure 601 is on the order of a wavelength of interest (e.g., a wavelength of light that may be detected to reveal the identification marking 600). The grating structure 601 is configured to reflect or diffract a specific color of light depending on an angle of incidence θ of the incident light L and the periodicity d of the grating structure 601. The wavelength of the light reflected or diffracted from the grating structure 601 is defined according to the grating equation as follows: $n\lambda = d(\sin\theta + \sin\theta')$, where n is the order of diffraction, λ is the diffracted wavelength, d is the periodicity of the grating structure 601 (e.g., the grating constant), θ is the angle of incidence of the incident light L measured from the grating normal, and θ' is the angle of diffraction measured from the grating normal. The presence of the identification marking 600 on the lens may be revealed or determined by directing incident light L toward the grating structure 601 at an angle of incidence θ, and detecting (e.g., viewing or measuring) the color of the light reflected or diffracted from the grating structure 601. In one or more embodiments, the grating structure 601 may be a reflective type grating structure or a transmissive type grating structure. In one or more embodiments, the grating structure 601 may be a ruled grating structure including a series of grooves arranged regularly with a periodicity or a holographic grating structure including sinusoidal grooves formed from a photosensitive (photoresist) material. In one or more embodiments, the grating structure 601 may include two or more different periodicities (e.g., the periodicity of the grating structure 601 may vary), which is configured to induce a change in the color of the light reflected or diffracted from the grating structure 601 for a fixed viewing angle. In this manner, providing the grating structure 601 with two or more different periodicities is configured to encode at least one additional degree of information (e.g., a non-binary value) compared to a grating structure 601 with a single periodicity. This embodiment of the identification marking is referred to herein as the "grating marking."

Figure 7:
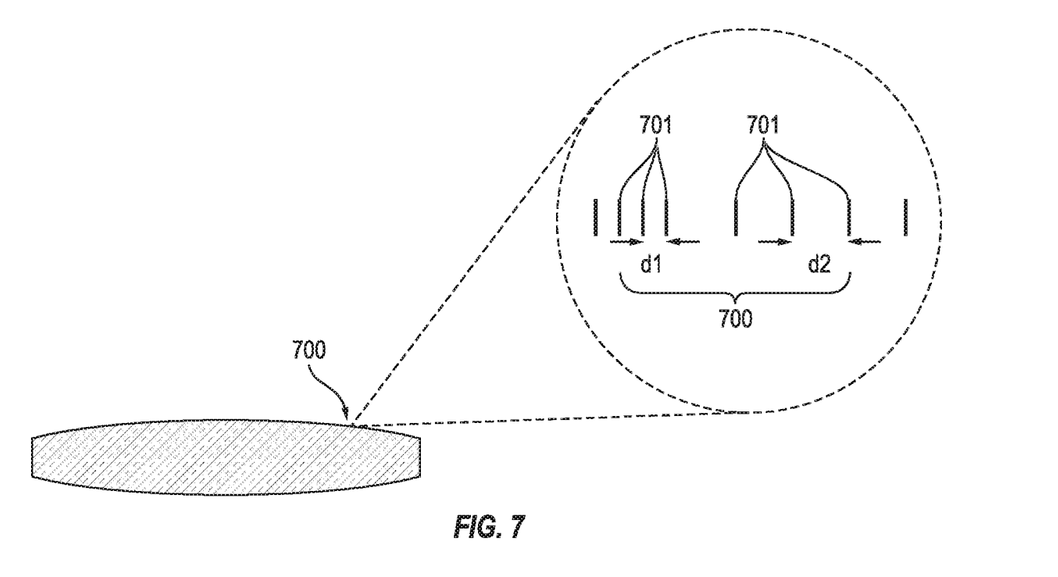
FIG. 7 is a front view of a lens including a Fourier marking according to one embodiment of the present disclosure.

With reference now to FIG. 7, an identification marking 700 according to one embodiment of the present disclosure includes a pattern of micro- or nano-structure features 701 having at least one periodicity (e.g., at least one pitch between adjacent features 701 of the pattern). In one or more embodiments, the pattern may be an array or a series. In one or more embodiments, the pattern of micro- or nano-structure features 701 may include two or more periodicities $d_1$, $d_2$ (e.g., a range of different periodicities). In one or more embodiments, the pattern of micro- or nano-structure features 701 may have at least one periodicity and two or more angles defined between adjacent micro- or nano-structure features 701 (e.g., variable angles defined between adjacent micro- or nano-structure features 701). In one or more embodiments, the features 701 may include lines (e.g., grooves or channels), dots, combinations of lines and dots, or any other suitable structure or combinations of structures. In one or more embodiments, the pattern of features 701 may be formed in or on an anterior surface of the lens, in or on a posterior surface of the lens, in or on an outer periphery (e.g., a perimeter or edge) of the lens, or in an interior portion (e.g., a bulk portion) of the lens between the anterior and posterior surfaces. The presence of the at least one identification marking 700 on the lens may be revealed or determined by taking an image (e.g., with a microscope) of the lens or at least a portion of the lens containing the identification marking 700 and performing a fast Fourier transform (FFT) on the image to transform the one or more periodicities $d_1$, $d_2$ of the pattern of features 701 into one or more points in the Fourier space (e.g., the one or more periodicities of the pattern of features are resolvable or readable in the Fourier space). For instance, in one embodiment in which the pattern includes a series of features 701 regularly arranged with a single periodicity, performing an FFT on an image of the pattern would produce a single data point or line corresponding to the periodicity of the features 701 in the pattern.

In one or more embodiments, the pattern of features is configured such that when light having a predetermined wavelength is incident on the pattern, a pattern is projected onto a screen at a specific distance or captured by an imaging system including one or multiple lenses. An FFT may then be performed on the projected pattern to transform the projected pattern into one or more points or lines readable in the Fourier space. Accordingly, the presence of the identification marking 700 on the lens may be revealed or determined by performing an FFT on an image of the pattern on the lens or by performing an FFT on a pattern projected onto a screen by directing light through the pattern on the lens. This embodiment of the identification marking is referred to herein as the "Fourier marking."

Figure 8A:
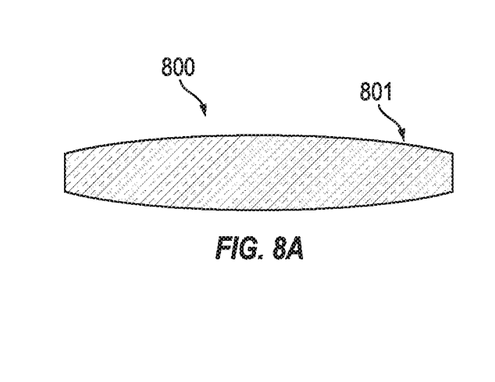
FIG. 8A is a front view of a lens including an array of cells according to one embodiment of the present disclosure.
Figure 8B:
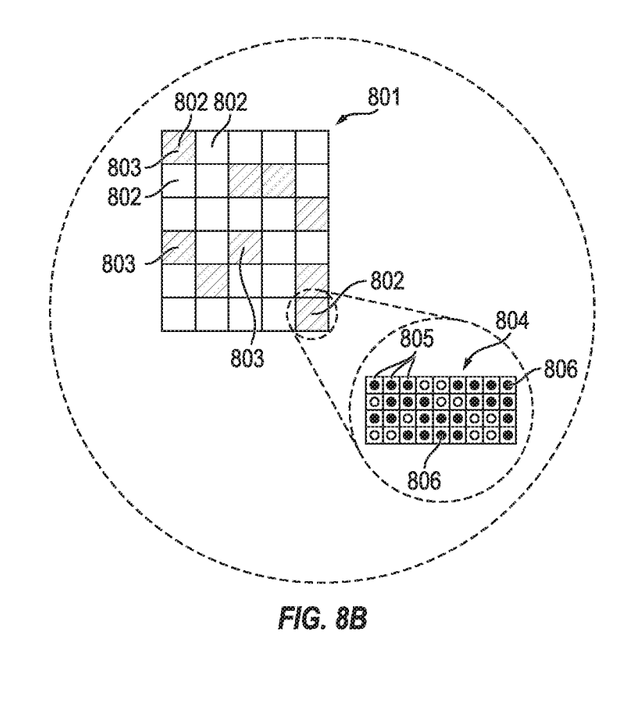
FIG. 8B is a front view of a super-structure in one of the cells of the embodiment of the array illustrated in FIG. 8A.

With reference now to FIGS. 8A-8B, a lens 800 according to one embodiment of the present disclosure includes an n×m array 801 (e.g., a matrix or a grid including n rows and m columns) including a series of cells 802. Although in the illustrated embodiment the array 801 is a 6×5 array (e.g., n=6 and m=5), in one or more embodiments, the array 801 may have any other suitable size. Each cell in the array 801 is either provided without any identification markings or provided with at least one identification marking 803. The array 801 may include a single type or kind of identification marking (e.g., the "phase plate marking" described above with reference to FIG. 2, the "Brewster angle marking" described above with reference to FIG. 3, the "retro-reflector marking" described above with reference to FIG. 4, the "pyramidal reflector marking" described above with reference to FIG. 5, the "grating marking" described above with reference to FIG. 6, or the "Fourier marking" described above with reference to FIG. 7) or a combination of two or more different types or kinds of identification markings.

In one or more embodiments, each cell 802 in the array 801 represents a bit (e.g., a binary value or digit of either 0 or 1). In one or more embodiments, the absence of any identification markings in a cell 802 represents a value of 0, and the presence of one or more identification markings 803 in a cell 802 represents a value of 1 or a value between 0 and 1. In one or more embodiments, the absence any identification markings in a cell 802 represents a value of 1 (or any value between 0 and 1), and the presence of one or more identification markings 803 in a cell 802 represents a value of 0. Together, the values of the cells 802 (e.g., 0 or 1) encode identification information, such as, for instance, optical characteristics of the lens (e.g., intraocular lens (IOL) type, power range, spherical equivalent (SE), cylinder power (Cyl), axis, spherical aberration (SA), and/or zonal information), a manufacturing process of the lens, and/or customer information (e.g., surgeon, clinic, patient, and/or shipping address). For instance, in the embodiment illustrated in FIG. 8A, the array 801 includes one or more identification markings 803 in cells 802 (1,1), (2,3), (2,4), (3,5), (4,1), (4,3), (5,2), (5,5), and (6,5), and together these bits encode identification information about the lens. In the illustrated embodiment in which the array 801 is a 6×5 array and each of the cells 802 in the array 801 represents a bit, the array 801 is configured to encode $2^{(6 \times 5)}$ (i.e., $2^{30}$) unique values or representations. In one or more embodiments, the array 801 may define a data matrix code or a matrix barcode (e.g., a two-dimensional bar code such as a QR code).

In one or more embodiments, one or more of the cells 802 of the array 801 may include a super-structure 804 having an array (e.g., a matrix) of sub-cells 805. Each sub-cell 805 in the super-structure 804 is provided either with or without an identification marking 806. Each cell 802 marked with a super-structure 804 is configured to represent a value of 0, a value of 1, or a series of different values between 0 and 1. The number of different values between 0 and 1 that the super-structure 803 is configured to represent depends on the number of sub-cells 805 and the structure (morphology) thereof in the super-structure 804. For instance, in the illustrated embodiment, the super-structure 804 includes a 9×4 array of sub-cells 805, and therefore the super-structure 804 is configured to represent $2^{(9 \times 4)}$ (i.e., $2^{36}$) different values between 0 and 1. In one or more embodiments, the super-structure 804 may be any other suitable size depending on the desired number of values that the super-structure 804 is configured to represent between 0 and 1. The identification markings 806 in the super-structure 804 may include a single type or kind of identification marking (e.g., any of the identification markings described above with reference to the embodiments illustrated in FIGS. 2-7) or a combination of two or more different types or kinds of identification markings.

In one or more embodiments, one or more of the cells 802 in the array 801 is configured to represent a value of 0, a value of 1, or a continuous range of values between 0 and 1. In one or more embodiments, the range of values that one or more of the cells 802 is configured to represent between 0 and 1 depends on the type or kind of marking in the cell 802, the quality of the marking (e.g., the accuracy and repeatability of the engraving method, including the dimensional tolerances, used to manufacture the marking), and/or the resolution of the instrument reading the marking (e.g., an interferometer). For instance, in one or more embodiments, one of the cells 802 of the array 801 may include the phase plate marking 200 described above with reference to FIG. 2, and the phase plate marking 200 is configured to represent any value between 0 and $2\pi$ radians depending on the depth d of the recessed surface 201 relative to wavelength of the incident light. In one or more embodiments, the number of values that the cell 802 including the phase plate marking 200 can represent between 0 and $2\pi$ radians is limited by the resolution of the interferometer reading the phase shift of the light induced by the phase plate marking 200. Similarly, in one or more embodiments, one or more of the sub-cells 805 in the super-structure 804 is configured to represent a value of 0, a value of 1, a continuous range of values between 0 and 1, or any value between 0 and $2\pi$ radians.

In one or more embodiments, the super structure 804 itself may define the range of values (e.g., between 0 and 1 or between 0 and $2\pi$ radians) that the super structure 804 is configured to represent as much as the number of sub-cells 805 in the super structure 804. Each cell 803 of the array 801 may be formed of a single marking or two or more markings (e.g., gratings, phase plates, etc.) each configured to represent a non-binary value (e.g., a value between 0 and 1 or between 0 and $2\pi$ radians). For instance, in one or more embodiments, a red reflection off of the grating marking 600 in one of the cells 803 may represent a value of 1 and no reflection off of the grating marking 600 may represent a value of 0. Any grating structure in the cell 803 that produces a color other than red (e.g., blue, green, or yellow) may be assigned a value between 0 and 1 (e.g., a value of 0.7, 0.8, and 0.55 for the blue, green, and yellow colors, respectively). Additionally, assuming a marked cell 802 represents a value of 1 and an unmarked cell 802 represents a value of 0, the combination of zeros and ones represented by the A×B matrix of sub-cells 805 in the superstructure 804 forms a "gray" value between 0 and 1. In this case, the marking that represents a 0 value and the marking that represents a 1 value are fixed, and the relative frequency of the ones and zeros represented by the sub-cells 805 in the superstructure 804 define a value between 0 and 1 (e.g., the relative frequency of the ones and zeros represented by the sub-cells 805 in the superstructure 804 define shades of "gray").

The markings of the present disclosure may be manufactured by any suitable micro- or nano-structuring process or processes, such as, laser engraving, lithography (e.g., UV or electron beam lithography), 3D printing, micro-milling, or combinations thereof. In one or more embodiments, the one or more markings of the present disclosure may be provided on an ophthalmic lens for the treatment of presbyopia, hyperopia, myopia, or cataracts, such as an IOL (e.g., a pseudophakic IOL, a phakic IOL, an aphakic IOL, or a toric IOL) or a contact lens. In one or more embodiments, the one or more markings of the present disclosure may be provided on any other suitable type of lens, for instance, optical elements for electronic devices. The lens or other optical element in which the one or more markings are engraved may be made of any material suitable for the application of the lens or other optical element, such as glass, plastic, metal, or a photovoltaic material. In one or more embodiments, the lens or other optical element may be made out of any suitable transparent or semi-transparent optical material. In one or more embodiments, the one or more markings may be provided on an ophthalmic lens made of any suitable biologically inert or biocompatible material, such as polymethylmethacrylate (PMMA), silicone, hydrophobic acrylate, or hydrophilic acrylate. In one or more embodiments in which the lens or other optical element is not utilized as an ophthalmic lens, the lens or other optical element may be made out of a non-transparent material (e.g., a translucent or opaque material).

Figure 9:
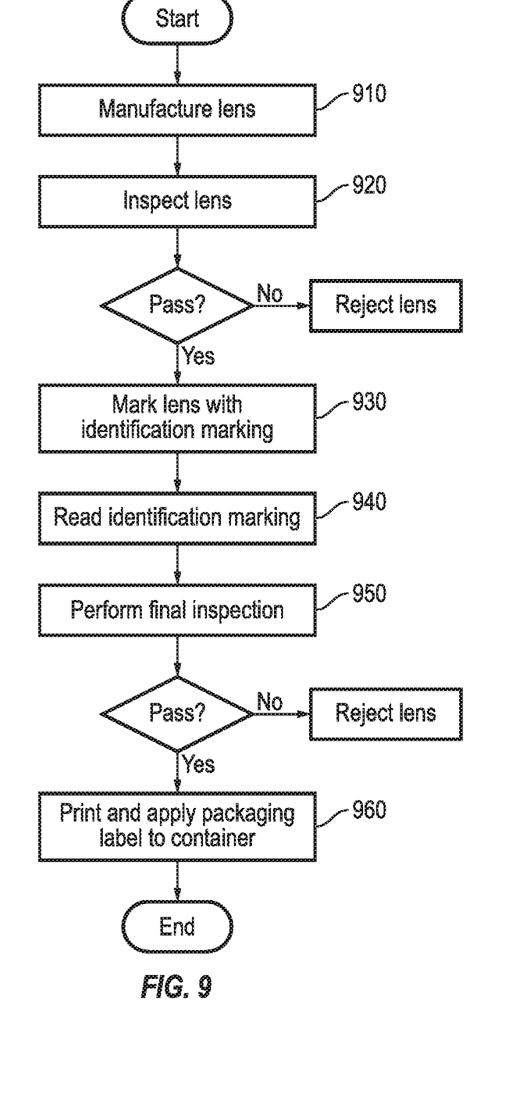
FIG. 9 is a flowchart illustrating tasks of a method according to one embodiment of the present disclosure.

With reference now to FIG. 9, a method 900 according to one embodiment of the present disclosure includes a task 910 of manufacturing a lens (e.g., an ophthalmic lens). In one or more embodiments, the task 910 of manufacturing the lens may include placing a bulk material utilized to manufacture the lens (e.g., the ophthalmic lens) in a container having a unique identification of the material and/or manufacturing data (e.g., manufacturing parameters) that will be utilized to manufacture the lens from the bulk material.

In one or more embodiments, the method 900 may include a task 920 of inspecting the lens (e.g., optically and/or dimensionally inspecting the lens). In one or more embodiments, the task 920 of inspecting the lens may be performed during the task 910 of manufacturing the lens (e.g., the lens may be optically and dimensionally inspected on aspects of the lens that do not change with further manufacturing processes) or after the task 910 of manufacturing the lens.

In the illustrated embodiment, the method 900 also includes a task 930 of marking the lens with at least one identification marking configured to identify one or more characteristics of the lens (e.g., an optical property of the lens, such as intraocular lens (IOL) type, power range, spherical equivalent (SE), cylinder power (Cyl), axis, spherical aberration (SA), and/or zonal information), a manufacturing process of the lens, and/or customer information (e.g., identification of the surgeon, the clinic, the patient, and/or a shipping address). The identification marking may be any suitable type of identification marking (e.g., the "phase plate marking" 200 described above with reference to FIG. 2, the "Brewster angle marking" 300 described above with reference to FIG. 3, the "retro-reflector marking" 400 described above with reference to FIG. 4, the "pyramidal reflector marking" 500 described above with reference to FIG. 5, the "grating marking" 600 described above with reference to FIG. 6, or the "Fourier marking" 700 described above with reference to FIG. 7). In one or more embodiments, the identification marking may be an array of identification marking as described above with reference to the embodiment illustrated in FIGS. 8A-8B. The array may include a single type of identification marking or a combination of two or more different types or kinds of identification markings. The task 930 of marking the lens may be performed during the task 910 of manufacturing the lens or after the task 910 of manufacturing the lens. The task of marking the lens with at least one identification marking may be performed by any suitable process or processes, such as laser engraving, lithography (e.g., UV or electron beam lithography), 3D printing, micro-milling, or combinations thereof.

In one or more embodiments, the task 930 of marking the lens may occur after the task 920 of inspecting the lens. In one or more embodiments, the task 930 of marking the lens may be performed only if the measurements determined during the task 920 of inspecting the lens are within acceptable specification limits (e.g., the measurement results pass the specification limits).

The identification marking on the lens, which may be formed during or after the task 910 of manufacturing the lens, may include the information provided on the container (e.g., the material properties of the bulk material and/or the manufacturing data identified on the container may be associated with the marking on the lens). In one or more embodiments, the identification on the container may be removed following the task 930 of marking the lens. Additionally, the identification marking on the lens may encode additional information (e.g., information not provided on the container) such as the optical properties of the lens.

In one or more embodiments, the task 930 of marking the lens with the identification marking may be performed during the task 910 of manufacturing the lens. Performing the task 930 of marking the lens with the identification marking during the task 910 of manufacturing the lens enables the lens to be formed as part of a batch process (e.g., a tumble polish process) with different types of lenses and/or lenses having different properties. That is, performing the task 930 of marking the lens during the task 910 of manufacturing the lens enables the utilization of manufacturing techniques in which the unique identification and/or tracking of the different lenses would not be possible without the identification markings on the lenses. In this manner, a relatively low cost batch manufacturing process may be utilized to manufacture the lenses of the present disclosure. Moreover, performing the task 930 of marking the lens with the identification marking during the task 910 of manufacturing the lens enables automation and automatic detection of the lens during the manufacturing process.

In one or more embodiments in which the lens is a toric IOL, the task 930 of marking the lens may include marking the lens to define an axis of the tonic IOL (e.g., an axis defining a flat meridian of the toric IOL) that is configured to be aligned with a patient's pre-existing astigmatism axis during Implantation of the toric IOL (e.g., the task 930 of marking the lens may include forming the markings 104, 105 illustrated in FIGS. 1A-1D).

The method 900 may also include a task 940 of reading the one or more identification markings on the lens. The task 940 of reading the one or more identification markings may be performed after the task 910 of manufacturing the lens is complete. The task 940 of reading the one or more identification markings may be performed in any suitable manner depending on the type or kind of identification marking, such as irradiating the lens and visually inspecting the lens with the naked eye, irradiating the lens and measuring a phase shift in the incident light with an interferometer, or imaging the one or more identification markings on the lens and performing a fast Fourier transform (FFT) to read the one or more identification markings in the Fourier space. The task 940 of reading the one or more identification markings on the lens may be performed to verify that the lens has the expected properties before use (e.g., before implantation in the capsular bag of the patient's eye). The task 940 of reading the one or more identification markings on the lens may be performed to reveal the origin of the lens (e.g., the manufacturing facility) and/or the manufacturing data (e.g., the manufacturing parameters) of the lens. For instance, if the lens is found without any accompanying identification (e.g., the lens is found outside of a labeled container), the one or more identification markings on the lens may be read to reveal the origin of the lens and/or the properties of the lens. In one or more embodiments, the task 940 of reading the one or more identification markings on the lens may be performed when the lens is cleaned and ready to be packaged.

The method may include a task 950 of performing a final inspection of the lens. In one or more embodiments, the task 950 of performing the final inspection may utilize a measurement system configured with the characteristics of the lens and/or the manufacturing process of the lens (e.g., specification limits and/or lighting settings) determined from the task 940 of reading the one or more identification markings on the lens. The task 950 of performing the final inspection of the lens may include an optical test and/or a cosmetic visual inspection.

If the lens passes the final inspection, the method may also include a task 960 of printing a packaging label including information linked or associated with the information encoded by the one or more identification markings on the lens (e.g., type of lens, optical properties of the lens, and/or a manufacturing process of the lens) applying the packaging label to a package (e.g., a container) containing the lens. In one or more embodiments, the packaging label may include customer information (e.g., identification of the surgeon, the clinic, the patient, and/or a shipping address) that was included as part of the order data. In one or more embodiments, one or more portions of the customer information may be concealed (e.g., covered) to safeguard the customer's privacy.

While this invention has been described in detail with particular references to exemplary embodiments thereof, the exemplary embodiments described herein are not intended to be exhaustive or to limit the scope of the invention to the exact forms disclosed. Persons skilled in the art and technology to which this invention pertains will appreciate that alterations and changes in the described structures and methods of assembly and operation can be practiced without meaningfully departing from the principles, spirit, and scope of this invention, as set forth in the following claims. Although relative terms such as "outer," "inner," "upper," "lower," "below," "above," and similar terms have been used herein to describe a spatial relationship of one element to another, it is understood that these terms are intended to encompass different orientations of the various elements and components of the invention in addition to the orientation depicted in the figures. Additionally, as used herein, the term "substantially," "about," and similar terms are used as terms of approximation and not as terms of degree, and are intended to account for the inherent deviations in measured or calculated values that would be recognized by those of ordinary skill in the art. Furthermore, as used herein, when a component is referred to as being "on" another component, it can be directly on the other component or components may also be present therebetween. Moreover, when a component is referred to as being "coupled" to another component, it can be directly attached to the other component or intervening components may be present therebetween.

What is claimed is:

1. A lens, comprising:
   an optic comprising:
      a posterior surface; and
      an anterior surface;
   a pair of haptics extending outward from the optic; and
   at least one identification marking on at least one haptic of the pair of haptics of the lens,
   wherein the at least one identification marking exhibits a first degree of visibility in an ambient lighting condition and a second degree of visibility greater than the first degree of visibility in a lighting condition different than the ambient lighting condition,
   wherein the at least one identification marking encodes information identifying at least one characteristic of the lens selected from the group consisting of a serial number, an optical property, a manufacturing process, and customer information,
   wherein the at least one identification marking comprises a micro-structure engraving or a nano-structure engraving, and
   wherein the micro-structure engraving or the nano-structure engraving of the at least one identification marking is invisible to the naked human eye in the ambient lighting condition.

2. The lens of claim 1, wherein:
   the lighting condition comprises incident light having a wavelength, and
   the at least one identification marking comprises a phase plate having a depth substantially equal to or less than the wavelength of the incident light.

3. The lens of claim 2, wherein the phase plate is configured to phase shift the incident light, and wherein the phase shift is detectable by an interferometer.

4. The lens of claim 1, wherein:
   the at least one identification marking comprises a flat surface and a tapered indent, and
   the lighting condition comprises polarized light angled at Brewster's angle with respect to the flat surface.

5. The lens of claim 4, wherein:
   the tapered indent comprises a step and a slanted surface,
   the slanted surface of the tapered indent is configured to reflect the polarized light, and
   the flat surface is configured not to reflect the polarized light.

6. The lens of claim 1, wherein the at least one identification marking comprises a retro-reflector.

7. The lens of claim 1, wherein the at least one identification marking comprises a pyramidal reflector.

8. The lens of claim 1, wherein the at least one identification marking comprises a diffraction grating.

9. The lens of claim 1, wherein the at least one identification marking comprises a plurality of identification markings.

10. The lens of claim 9, wherein a first identification marking of the plurality of identification markings is at least partially aligned with a second identification marking of the plurality of identification markings along an axis parallel to an optical axis of the lens, and wherein the first identification marking and the second identification markings are at different positions along the axis.

11. A lens, comprising:
    an optic comprising:
       a posterior surface; and
       an anterior surface;
    a pair of haptics extending outward from the optic; and
    at least one identification marking on at least one haptic of the pair of haptics of the lens, wherein the at least one identification marking comprises a pattern of features having at least one periodicity resolvable in Fourier space, wherein the pattern of features is an array comprising a first plurality of features having a first periodicity and a second plurality of features having a second periodicity different than the first periodicity adjacent to the first plurality of features of the pattern, wherein at least two different angles are defined between adjacent features in the first plurality of features and the second plurality of features.

12. The lens of claim 11, wherein the at least one periodicity comprises three or more different periodicities.

13. The lens of claim 11, wherein each feature of the pattern of features is a micro-structure engraving or a nano-structure engraving.

14. The lens of claim 13, wherein each feature of the pattern of features is a line or a dot.

15. A lens, comprising:
a posterior surface;
an anterior surface;
a matrix comprising a plurality of cells configured to encode identification information of the lens; and
at least one identification marking in at least one cell of the plurality of cells, the at least one identification marking comprising a micro-structure engraving or nano-structure engraving, wherein the at least one cell of the plurality of cells comprises a super-structure, the super-structure comprising a plurality of sub-cells arranged in a sub-matrix.

16. The lens of claim 15, wherein the at least one identification marking comprises a phase plate.

17. The lens of claim 15, wherein the at least one identification marking comprises a flat surface and a tapered indent.

18. The lens of claim 15, wherein the at least one identification marking comprises a retro-reflector.

19. The lens of claim 15, wherein the at least one identification marking comprises a pyramidal reflector.

20. The lens of claim 15, wherein the at least one identification marking comprises a diffraction grating.

21. The lens of claim 15, wherein the at least one identification marking comprises a pattern of features having at least one periodicity resolvable in Fourier space.

22. The lens of claim 15, wherein each cell of the plurality of cells in the matrix represents a binary digit of the encoded identification information, wherein each cell without an identification marking represents one of a value of 0 or a value of 1, and wherein each cell comprising at least one identification marking represents the other of the value of 0 and the value of 1.

23. The lens of claim 15, wherein at least one cell of the plurality of cells comprising the at least one identification marking represents a non-binary value of the encoded identification information.

24. The lens of claim 23, wherein the non-binary value is in a range from 0 to 1.

25. The lens of claim 23, wherein the non-binary value is in a range from 0 to $2\pi$ radians.

26. The lens of claim 15, further comprising a first type of identification marking in one cell of the plurality of cells and a second type of identification marking different than the first type of identification marking in another cell of the plurality of cells.

27. The lens of claim 15, wherein the matrix defines a data matrix code or a matrix barcode.

28. The lens of claim 15, wherein the at least one identification marking comprises human readable text or machine readable text.

* * * * *